(12) United States Patent  
Hosaka et al.

(10) Patent No.: US 6,740,371 B1
(45) Date of Patent: May 25, 2004

(54) DIAMINOBENZENE DERIVATIVE, POLYIMIDE OBTAINED THEREFROM, AND LIQUID-CRYSTAL ALIGNMENT FILM

(75) Inventors: Kazuyoshi Hosaka, Chiba (JP); Hideyuki Nawata, Chiba (JP); Takayasu Nihira, Chiba (JP); Hideyuki Isogai, Chiba (JP); Hideyuki Endou, Chiba (JP); Hiroyoshi Fukuro, Chiba (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/018,860

(22) PCT Filed: Jun. 28, 2000

(86) PCT No.: PCT/JP00/04250

§ 371 (c)(1),
(2), (4) Date: Dec. 26, 2001

(87) PCT Pub. No.: WO01/02466

PCT Pub. Date: Jan. 11, 2001

(30) Foreign Application Priority Data

Jun. 30, 1999 (JP) .......................................... 11/185164

(51) Int. Cl.⁷ ........................ C09K 19/02; B32B 27/00; C08G 73/10; G02F 1/1337
(52) U.S. Cl. .................... 428/1.2; 428/1.26; 428/473.5; 528/125; 528/128; 528/170; 528/172; 528/173; 528/174; 528/179; 528/183; 528/185; 528/220; 528/188; 528/229; 528/350; 528/353
(58) Field of Search ................................ 528/125, 128, 528/170, 172, 173, 174, 179, 183, 185, 220, 229, 350, 353, 188, 171; 428/1.2, 1.26, 473.5; 564/442

(56) References Cited

U.S. PATENT DOCUMENTS

| 6,111,059 A | * | 8/2000 | Nihira et al. ................. 528/353 |
| 6,500,913 B2 | * | 12/2002 | Mathew et al. ............. 528/170 |

FOREIGN PATENT DOCUMENTS

| EP | 0 772 074 | | 5/1997 |
| JP | 5-117211 | | 5/1993 |
| JP | 5-294903 | | 11/1993 |
| JP | 5-301849 | | 11/1993 |
| JP | 6-16597 | | 1/1994 |
| JP | 6-16601 | | 1/1994 |
| JP | 6-145347 | | 5/1994 |
| JP | 11-181090 | | 7/1999 |
| JP | 11-202339 | | 7/1999 |
| JP | 11-269267 | | 10/1999 |
| JP | 11-302376 | | 11/1999 |
| JP | 2000-80164 | | 3/2000 |
| JP | 02001072770 A | * | 3/2001 |
| JP | 02001160493 A | * | 6/2001 |
| WO | WO 98/02776 | | 1/1998 |
| WO | 98/02776 | | 1/1998 |
| WO | WO 99/28783 | | 6/1999 |

OTHER PUBLICATIONS

G. Yang, et al., Macromolecules, vol. 32, No. 7, pp. 2215–2220, XP–002217081, "Synthesis and Properties of Hyperbranched Aromatic Polyamide", Apr. 6, 1999.

G. C. Eastmond, et al., Derwent Publications, AN 1998:376601, pp. 1–2, XP–002217072, "Methyl–and Fluoro–Substituted BIS (4–Aminophenoxy)Benzenes. A Convient Method of Synthesis", 1998.

M. V. Dorogov, et al., Derwent Publications, AN 1997:130855, pp. 1–2, XP–002217083, "Synthesis of Symmetric Aromatic Diamines with Two Ester Bridge Groups", 1996.

Derwent Publications, AN 1993:603174, pp. XP–002217084, JP 5–140072, Jun. 8, 1993.

(List continued on next page.)

*Primary Examiner*—P. Hampton-Hightower
(74) *Attorney, Agent, or Firm*—Oblon, Spivak, McClelland, Maier & Neustadt, P.C.

(57) ABSTRACT

An alkyldiamine having excellent polymerization reactivity, a polyimide comprising it as a constituting element, and a liquid crystal alignment film excellent in uniformity of liquid crystal alignment, are presented. Namely, the present invention relates to a diaminobenzene derivative represented by the following general formula (1) and to a polyimide obtained by reacting a diamine containing at least 1 mol % of the diaminobenzene derivative represented by the general formula (1), with at least one compound selected from a tetracarboxylic. dianhydride and its derivatives, to obtain a polyimide. precursor having a reduced viscosity of from 0.05 to 5.0 dl/g (in N-methylpyrrolidone at a temperature of 30° C., concentration: 0.5 g/dl) and ring-closing it, and having a repeating unit represented by the general formula (2). Further, the present invention relates to a liquid crystal alignment film containing at least 1 mol % of the above repeating unit.

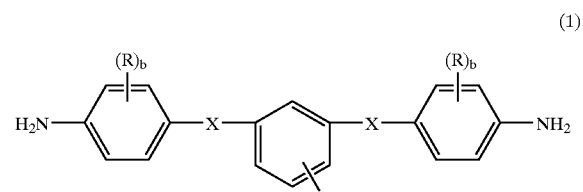

(1)

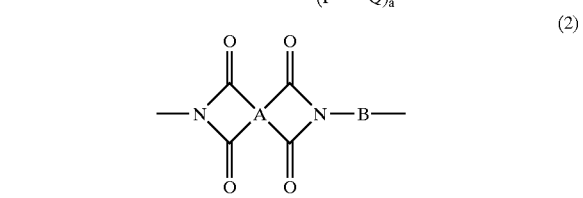

(2)

17 Claims, No Drawings

OTHER PUBLICATIONS

E. V. Shelud'ko, et al., Derwent Publications, AN 1987:197077, pp. 1–2, XP–002217085, "Fluorine–Containing Polyamide–Polyimides with Perfluoroalky and Polyfluoroalkoxyl Groups", 1987.

A. N. Nikolaeskii, et al., Derwent Publications, AN 1987:195716, pp. 1–2, XP–002217086, "Diamines of Polyphenyl Oxides as Inhibitors of Liquid–Phase Oxidation of Hydrocarbons", 1986.

B. F. Malichenko, et al., Derwent Publications, AN 1984:34921, pp. 1–4, XP–002217087, "Fluorine–Containing Ordered Copolyamides", 1983.

Patent Abstracts of Japan, JP 7–49501, Feb. 21, 1995.

J. Matraszek, et al., Derwent Publications, AN 2000:365493, pp. 1–2, XP–002217088, "Nematic Phase Formed by Banana–Shaped Molecules", 2000.

* cited by examiner

DIAMINOBENZENE DERIVATIVE, POLYIMIDE OBTAINED THEREFROM, AND LIQUID-CRYSTAL ALIGNMENT FILM

TECHNICAL FIELD

The present invention relates to a novel diaminobenzene derivative, a polyimide synthesized by using the compound as one of stating materials, and a liquid crystal alignment film containing the polyimide. More particularly, it relates to a diamine having a specific structure, which is industrially readily producible, a polyimide employing it, and a liquid crystal alignment film. The polyimide synthesized by using the diamine of the present invention, is particularly useful for an alignment film of a liquid crystal display device.

BACKGROUND ART

Heretofore, polyimides have been widely used as protecting materials or insulating materials in the electric and electronic fields, by virtue of high mechanical strength, heat resistance and solvent resistance, as their characteristics. However, developments in the electric and electronic fields in recent years have been remarkable, and increasingly high properties have been required also for materials to be used. Especially in the application to alignment films for liquid crystal display devices, polyimides have been mainly employed because of the uniformity and durability of the coating film surface. However, in an attempt for high densification and high performance of liquid crystal displays, the surface properties of polyimide coating films have become important, and it has become necessary to impart a new property which conventional polyimides do not have.

A liquid crystal display device is a display device utilizing an electro-optical change of liquid crystal and has undergone a remarkable development as a display device for various displays in recent years in view of the characteristics such that it is small in size and light in weight as a device and its power consumption is small. Especially, a twisted nematic type (TN-type) electric field effect liquid crystal display device is a typical example, wherein nematic liquid crystal having positive dielectric anisotropy is employed so that liquid crystal molecules are aligned in parallel with a substrate at the interface of each of a pair of mutually opposing electrode substrates, and the two substrates are combined so that the directions for alignment of liquid crystal molecules are orthogonal to each other.

In such a TN-type liquid crystal display device, it is important that long axis directions of liquid crystal molecules are aligned uniformly in parallel with the substrate surface and further that the liquid crystal molecules are aligned with a certain inclined alignment angle (hereinafter referred to as a tilt angle) against the substrate. As typical methods for aligning liquid crystal molecules in such a manner, two methods have been known heretofore.

The first method is a method which comprises vapor depositing an inorganic substance such as silicon oxide from an oblique direction to a substrate to form an inorganic film on the substrate, so that the liquid crystal molecules are aligned in the direction of vapor deposition. This method is not industrially efficient, although uniform alignment with a constant tilt angle can be obtained.

The second method is a method which comprises forming an organic coating film on a substrate surface, and rubbing its surface in a predetermined direction with a cloth of e.g. cotton, nylon or polyester, so that liquid crystal molecules are aligned in the rubbing direction. By this method, constant alignment can be obtained relatively easily, and industrially, this method is primarily employed. As the organic film, polyvinyl alcohol, polyoxyethylene, polyamide or polyimide may, for example, be mentioned. However, from the viewpoint of the chemical stability, thermal stability, etc., polyimide is most commonly employed.

In the field of liquid crystal alignment films, it has been difficult to obtain a high tilt angle constantly by the method of rubbing an organic film such as polyimide. As a means to solve such difficulty, JP-A-62-297819 proposes a treating agent for liquid crystal alignment made of a mixture of a long chain alkyl compound with a polyimide precursor. Further, JP-A-64-25126 discloses a treating agent for liquid crystal alignment made of a polyimide using, as a starting material, a diamine having an alkyl group. Thus, many attempts have been made to increase the tilt angle of liquid crystal by introducing an alkyl group into polyimide, and it has been made possible to increase the tilt angle.

In recent years, there have been remarkable developments in the TN display device, and many new properties are now required also for a liquid crystal alignment film. Among them, it has been increasingly important to satisfy stabilization of the tilt angle and improvement in the uniformity of alignment simultaneously, from the viewpoint of improvement of the essential properties of the liquid crystal alignment film. As is evident also from JP-A-64-25126, an alkyl diamine which has been heretofore been known and mainly used, is characterized in that an alkyl group is connected to a phenylene diamine structure. However, if a conventional alkyl group-containing diamine is employed, there has been a problem that when a polyimide is to be synthesized, the alkyl group acts as a steric hindrance, whereby the reactivity tends to be low, and it takes time for polymerization, or in some cases, polymerization does not proceed substantially. Taking time for the polymerization is problematic from the viewpoint of the industrial production, and the low polymerization reactivity is problematic from the viewpoint of the durability as an alignment film of polyimide. Further, when copolymerization with another diamine is carried out, such a low reactivity brings about a difference in the reaction rate. The resulting polyimide is not necessarily uniform form the viewpoint of the uniformity of the repeating units. Consequently, when it is made into a liquid crystal alignment film, even if a desired tilt angle may be obtained, the film has not necessarily been satisfactory from the viewpoint of the uniformity of liquid crystal alignment.

These problems are extremely important subjects to be solved to further improve the properties of a high quality, high precision liquid crystal display device represented by a future TN device. Namely, it has been desired to develop an alkyl diamine having an excellent reactivity, a polyimide containing it as a constituting element and a polyimide liquid crystal orientation film, which contribute to the solution of such problems.

DISCLOSURE OF THE INVENTION

The present invention has been made under the above circumstances. The present inventors have conducted extensive studies in detail and systematically to accomplish the above object, and as a result, have completed the present invention.

Namely, the present invention relates to a diaminobenzene derivative represented by the general formula (1):

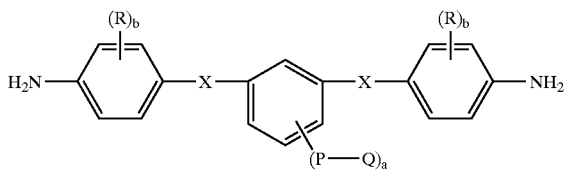

(wherein each of X and P which are independent of each other, is a single bond or a bivalent organic group selected from —O—, —COO—, —OCO—, —CONH— and —NHCO—, Q is a $C_{1\text{-}22}$ straight chain alkyl group or straight chain fluoroalkyl group, a is an integer of from 1 to 4 and represents the number of substituents, R is a substituent selected from fluorine, a methyl group and a trifluoromethyl group, and b is an integer of from 0 to 4 and represents the number of substituents).

Further, the present invention relates to a polyimide obtained by reacting a diamine containing at least 1 mol % of a diaminobenzene derivative represented by the general formula (1):

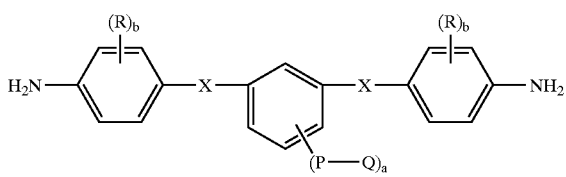

(wherein each of X and P which are independent of each other, is a single bond or a bivalent organic group selected from —O—, —COO—, —OCO—, —CONH— and —NHCO—, Q is a $C_{1\text{-}22}$ straight chain alkyl group or straight chain fluoroalkyl group, a is an integer of from 1 to 4 and represents the number of substituents, R is a substituent selected from fluorine, a methyl group and a trifluoromethyl group, and b is an integer of from 0 to 4 and represents the number of substituents), with at least one compound selected from a tetracarboxylic dianhydride and its derivatives, to obtain a polyimide precursor having a reduced viscosity of from 0.05 to 5.0 dl/g (in N-methylpyrrolidone at a temperature of 30° C., concentration: 0.5 g/dl) and ring-closing it, and having a repeating unit represented by the general formula (2):

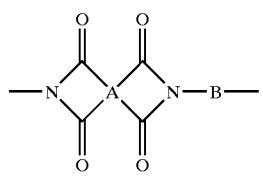

(wherein A is a tetravalent organic group constituting a tetracarboxylic acid, and B is a bivalent organic group constituting a diamine).

Still further, the present invention relates to a liquid crystal alignment film containing the above polyimide.

Now, the present invention will be described in detail.

The diaminobenzene derivative of the present invention can be easily synthesized and is useful as a starting material for e.g. a polyimide or a polyamide. Further, this may be used as one of starting materials to a obtain a polyimide having an alkyl group or a fluoroalkyl group as a side chain. This polyimide is useful for e.g. an insulating film for a semiconductor or a heat resistant protective film for an optical device, but is particularly useful as an alignment film for a liquid crystal display device, and it has excellent characteristics such that not only polymerization is quick at the time of the preparation of a polyimide precursor, but also a high tilt angle can easily be provided, and alignment of liquid crystal is good.

Particularly, the present invention has an important object to obtain a polyimide having a desired repeating unit quickly by using a specific diaminobenzene derivative having an alkyl group and to realize uniformity of alignment and a high tilt angle imparted to liquid crystal, by using the specific polyimide obtainable from the diamine, as a liquid crystal alignment film. For this purpose, Q in the general formula (1) is a $C_{1\text{-}22}$ straight chain alkyl group. This is essential to control the degree of the tilt-angle, and such a group is connected to the polyimide main chain via a connecting portion P. Further, X is essential to connect a p-aminophenyl group. Further, R is necessary to control the surface property of the polyimide within a range not to impair the nucleophilic nature of an amino group, when a polymerization reactivity with a tetracarboxylic dianhydride and its derivative is taken into consideration.

The diaminobenzene derivative represented by the general formula (1):

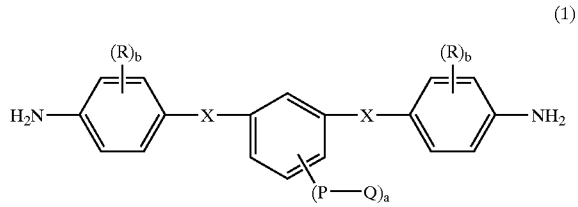

(wherein each of X and P which are independent of each other, is a single bond or a bivalent organic group selected from —O—, —COO—, —OCO—, —CONH— and —NHCO—, Q is a $C_{1\text{-}22}$ straight chain alkyl group or straight chain fluoroalkyl group, a is an integer of from 1 to 4 and represents the number of substituents, R is a substituent selected from fluorine, a methyl group and a trifluoromethyl group, and b is an integer of from 0 to 4 and represents the number of substituents), is a diamine having a specific structure, and it comprises the following two amine portions:

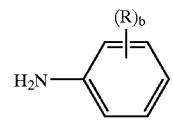

(wherein R and b are the same as in the formula (1)), a connecting portion X and the following alkyl or fluoroalkylbenzene portion:

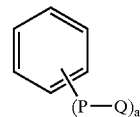

(wherein P, Q and a are the same as in the formula (1)). Its synthetic method is not particularly limited. For example, it can be synthesized by the following method.

Namely, in a synthesis of a diamine, it is common to synthesize the corresponding dinitro compound represented by the general formula (3):

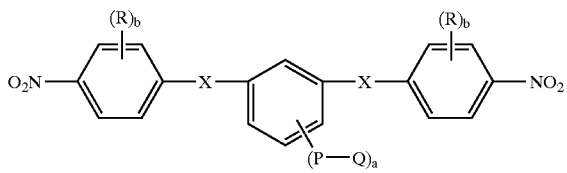 (3)

(wherein X, P, Q, a and b are the same as in the formula (1)), and to reduce the nitro groups by a usual method to convert them into amino groups.

Here, each of a and b which are independent of each other, represents the number of substituents; a is selected from integers of from 1 to 4 but is preferably 1 or 2 from the viewpoint of the surface property; and b is likewise selected from integers of from 0 to 2.

Each of connecting portions X and P which are independent of each other, is a connecting group such as a single bond, an ether bond —O—, an ester bond —COO—, a reverse ester bond —OCO—, an amide bond —CONH— or a reverse amide bond —NHCO—. From the viewpoint of the polymerization reactivity, an ether bond, an ester bond or an amide bond is particularly preferred.

Such a connecting group can be formed by a usual organic synthetic method. For example, in the case of an ether bond, it is common to react the corresponding halogen derivative and hydroxyl group-substituted derivative in the presence of an alkali, and in the case of an amide bond, it is common to react the corresponding acid chloride and amino group-substituted derivative in the presence of an alkali. Further, for the single bond, various methods are available, and common organic synthetic methods such as a Grignard reaction, a Friedel-Crafts acylation method of an aromatic ring, a Kishner reduction method and a cross coupling method, may be employed to suitably carry out the connection.

A specific example of the material for forming the dinitro moiety, is a benzene containing substituent Q and connecting group P, di-substituted by substituents for forming the connecting portions X such as halogen atoms, hydroxyl groups, amino groups, carboxyl groups, halogenated acyl groups or carbonyl groups, and such a benzene is connected to a substituted p-nitro benzene derivative to obtain a desired dinitro compound.

Specific examples of the di-substituted benzene derivative include 3,5-dihydroxybenzoic acid, 3,5-dihydroxybenzoic acid chloride, 3,5-dicarboxyphenol, 3,5-diaminobenzoic acid and 3,5-diaminophenol. Further, the p-nitrobenzene derivative may, for example, be p-nitrofluorobenzene, p-nitrochlorobenzene, p-nitrobromobenzene, p-nitroiodobenzene, p-nitrophenol, p-nitrobenzoic acid, p-nitrobenzoic acid chloride, 2-methyl-4-nitrophenol, 2-trifluoromethyl-4-nitrophenol, 2-methyl-4-nitrobenzoic acid, 2-methyl-4-nitrobenzoic acid chloride, 2-trifluoromethyl-4-nitrobenzoic acid, 2-trifluoromethyl-4-nitrobenzoic acid chloride or acetanilide. A combination thereof may be suitably selected depending upon the particular purpose taking into consideration the reactivity and the availability of the materials. It should be mentioned that those exemplified here are only examples.

The chain substituent Q in the general formula (1) is a $C_{1-22}$ straight chain alkyl group or straight chain fluoroalkyl group. The carbon number can be suitably selected in order to obtain the desired tilt angle when the corresponding polyimide is used as an alignment film.

The diaminobenzene derivative of the present invention represented by the above general formula (1) obtainable by the method as described above, may be subjected to polycondensation with a tetracarboxylic acid dianhydride and its derivative, such as tetracarboxylic dianhydride, a tetracarboxylic dihalide or tetracarboxylic acid, to synthesize a polyimide having a specific structure at its side chain.

The method for obtaining the polyimide of the present invention, is not particularly limited. Specifically, it can be obtained by reacting and polymerizing the above diamine with at least one compound selected from a tetracarboxylic dianhydride and its derivatives, to obtain a polyimide precursor, followed by ring-closing imide conversion.

The tetracarboxylic dianhydride and its derivatives to be used to obtain the polyimide of the present invention, are not particularly limited.

Specific examples thereof include aromatic tetracarboxylic dianhydrides such as pyromellitic dianhydride, 2,3,6,7-naphthalene tetracarboxylic dianhydride, 1,2,5,6-naphthalene tetracarboxylic dianhydride, 2,3,6,7-anthracene tetracarboxylic dianhydride, 1,2,5,6-anthracene tetracarboxylic dianhydride, 3,3',4,4'-biphenyl tetracarboxylic dianhydride, 2,3,3',4-biphenyl tetracarboxylic dianhydride, bis(3,4-dicarboxyphenyl)ether dianhydride, 3,3',4,4'-benzophenone tetracarboxylic dianhydride, bis(3,4-dicarboxyphenyl)sulfone dianhydride, bis(3,4-dicarboxyphenyl)methane dianhydride, 2,2-bis(3,4-dicarboxyphenyl)propane dianhydride, 1,1,1,3,3,3-hexafloro-2,2-bis(3,4-dicarboxyphenyl)propane dianhydride, bis(3,4-dicarboxyphenyl)dimethyl silane dianhydride, bis(3,4-dicarboxyphenyl)diphenyl silane dianhydride, 2,3,4,5-pyridine tetracarboxylic dianhydride, and 2,6-bis(3,4-dicarboxyphenyl)pyridine dianhydride, and their tetracarboxylic acids and their dicarboxylic acid diacid halides; alicyclic tetracarboxylic dianhydrides such as 1,2,3,4-cyclobutane tetracarboxylic dianhydride, 1,2,3,4-cyclopentane tetracarboxylic dianhydride, 1,2,4,5-cyclohexane tetracarboxylic dianhydride, 2,3,5-tricarboxycyclopentyl acetic dianhydride, and 3,4-dicarboxy-1,2,3,4-tetrahydro-1-naphthalene succinic dianhydride, and their tetracarboxylic acids and their dicarboxylic acid diacid halides; and aliphatic tetracarboxylic dianhydrides such as 1,2,3,4-buthane tetracarboxylic dianhydride, and their tetracarboxylic acids and their dicarboxylic acid diacid halides.

Especially for application to alignment films, alicyclic tetracarboxylic dianhydrides, and their tetracarboxylic acids and their dicarboxylic acid diacid halides are preferred from the viewpoint of the transparency of the coating film. Particularly preferred are 1,2,3,4-cyclobutane tetracarboxylic dianhydride, 3,4-dicarboxy-1,2,3,4-tetrahydro-1-naphthalene succinic dianhydride, bicyclo[3,3,0]-octane-tetracarboxylic dianhydride and 3,5,6-tricarboxynorbornane-2:3,5:6 dianhydride. Further, one or more of these tetracarboxylic dianhydrides and their derivatives may be used in admixture.

In the present invention, the tetracarboxylic dianhydride and its derivative may be copolymerized with the diaminobenzene derivative represented by the general formula (1) (hereinafter referred to simply as the diamine(1)) and other common diamines (hereinafter referred to simply as common diamines).

The common diamines to be used here are primary diamines commonly used for the synthesis of polyimides, and they are not particularly limited. Specific examples thereof include aromatic diamines such as p-phenylenediamine, m-phenylenediamine, 2,5-diaminotoluene, 2,6-diaminotoluene, 4,4'-diaminobiphenyl, 3,3'-dimethyl-4,4'-diaminobiphenyl, 3,3'-dimetoxy-4,4'-diaminobiphenyl, diaminodiphenylmethane, diaminodiphenyl ether, 2,2'-diaminodiphenylpropane, bis(3,5-diethyl-4-aminophenyl)methane, diaminodiphenylsulfone, diaminobenzophenone, diaminonaphthalene, 1,4-bis(4-aminophenoxy)benzene, 1,4-bis(4-aminophenyl)benzene, 9,10-bis(4-aminophenyl)anthracene, 1,3-bis(4-aminophenoxy)benzene, 4,4'-bis(4-aminophenoxy)diphenylsulfone, 2,2-bis[4-(4-aminophenoxy)phenyl]propane, 2,2-bis(4-aminophenyl)hexafluropropane and 2,2-bis[4-(4-aiminophenoxy)phenyl]hexafluropropane; aliphatic diamines such as bis(4-aminocyclohexyl)methane and bis(4-amino-3-methylcyclohexyl)methane, and aliphatic diamines such as tetramethylenediamine and hexamethylenediamine; as well as diaminocycloxanes such as

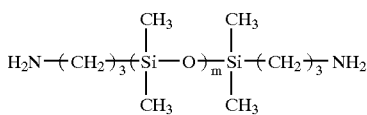

(wherein m is an integer of from 1 to 10). Further, these diamines may be used alone or in combination as a mixture of two or more of them.

By adjusting the proportion of the molar amount of the diamine (1) in the total molar amount of diamines used at the time of polymerization of the polyimide of the present invention, the surface property of the polyimide such as water repellency can be modified, and further in a case where it is used as a liquid crystal alignment film, wettability with liquid crystal, and further, the tilt angle of liquid crystal, can be increased. The proportion of the molar amount of the diamine (1) in the total molar amount of diamines to be used here, is at least 1 mol %.

Further, when it is used as a liquid crystal alignment film, it is common to adjust the proportion of the molar amount of the diamine (1) in the total molar amount of diamines to be used, to be within a range of from 1 mol % to 100 mol % from such a viewpoint that a polyimide having a practically suitable degree of polymerization can easily be obtained, or that the tilt angle required in a common liquid crystal display system (such as a twisted nematic system) is usually at a level of from a few degrees to about 10 degrees in many cases, although it may depend also on the number of alkyl of Q. Further, in the case of a perpendicular alignment system, the molar amount of the diamine (1) is usually from 40 mol % to 100 mol %.

The tetracarboxylic dianhydride and its derivative, and the above mentioned diamine, are reacted and polymerized to obtain a polyimide precursor, and then this is converted to an imide by ring closure. As the tetracarboxylic dianhydride and its derivative to be used here, it is common to employ tetracarboxylic dianhydride. The ratio of the molar amount of the tetracarboxylic dianhydride to the total molar amount of the diamine (1) and common diamines, is preferably from 0.8 to 1.2. Like in a usual polycondensation reaction, the polymerization degree of the resulting polymer tends to be large, as the molar ratio becomes close to 1.

If the polymerization degree is too small, the strength of the polyimide film tends to be inadequate. On the other hand, if the polymerization degree is too large, the operation efficiency at the time of formation of the polyimide film tends to be poor in some cases. Accordingly, the polymerization degree of the product in this reaction is preferably from 0.05 to 5.0 dl/g (in N-methylpyrrolidone at a temperature of 30° C., concentration: 0.5 g/dl) as calculated as the reduced viscosity of the polyimide precursor solution.

A method for reacting and polymerizing the carboxylic dianhydride and the above diamine, is not particularly limited. It is common to employ a method wherein the above diamine is dissolved in an organic polar solvent such as N-methylpyrrolidone, N,N-dimethylacetamide or N,N-dimethylformamide, and to the solution, the tetracarboxylic dianhydride is added and reacted to synthesize a polyimide precursor, followed by dehydration ring closure for conversion to an imide.

The reaction temperature at the time of the reacting the tetracarboxylic dianhydride and the above mentioned diamine to obtain a polyimide precursor, may be an optional temperature selected within a range of from −20 to 150° C., preferably from −5 to 100° C. Further, this polyimide precursor is subjected to dehydration under heating at a temperature of from 100 to 400° C., or subjected to chemical imide-conversion by means of an imide-conversion catalyst such as pyridine/acetic anhydride, which is commonly used, to obtain a polyimide. In such a case, the imide conversion can be controlled optionally within a range of from 0 to 100% by reaction conditions. In an application to an alignment film, the imide conversion is preferably from 60 to 100%.

When the polyimide of the present invention is to be used as an insulating film or a protecting film for an electric or electronic element, or as an alignment film for a liquid crystal display device, it is necessary to form a polyimide coating film having a uniform film thickness on a substrate.

To form this polyimide coating film, it is usually possible to form a polyimide coating film by coating the polyimide precursor solution by itself on a substrate and heating it for imide-conversion on the substrate. The polyimide precursor solution to be used here may be the above polymer solution by itself, or the formed polyimide precursor may be put into a large excess amount of a poor solvent such as water or methanol to precipitate and recover it, and then it may be used as re-dissolved in a solvent. The solvent for diluting the above polyimide precursor solution and/or the solvent for re-dissolving the precipitated and recovered polyimide precursor, is not particularly limited so long as it is capable of dissolving the polyimide precursor.

Specific examples of such solvents include N-methylpyrrolidone, N,N-dimethylacetoamide, and N,N-dimethylformamide. These solvents may be used alone or as mixed. Further, even in the case of a solvent which is incapable of presenting a uniform solution by itself, such a solvent may be added and used within a range where a uniform solution can be obtained. As such an example, ethyl cellosolve, butyl cellosolve, ethyl carbitol, butyl carbitol, ethyl carbitol acetate or ethylene glycol may be mentioned. Further, for the purpose of improving the adhesion of the polyimide film to the substrate, it is of course preferred to add an additive such as a coupling agent to the obtained polyimide precursor solution. Further, an optional temperature within a range of from 100 to 400° C. may be employed as the temperature for heating for imide-conversion on the substrate. However, particularly preferred is within a range of from 150 to 350° C.

On the other hand, in a case where the polyimide of the present invention is soluble in a solvent, the polyimide precursor obtained by the reaction of the tetracarboxylic dianhydride and the above mentioned diamine, may be imide-converted in the solvent to obtain a polyimide solution. To convert the polyimide precursor to a polyimide in the solution, it is common to employ a method wherein dehydration ring-closure is carried out by heating. This ring closure temperature by dehydration under heating may be an optional temperature selected within a range of from 150 to 350° C., preferably from 120 to 250° C. As another method for converting the polyimide precursor to the polyimide, it is possible to carry out ring closure chemically by means of a known dehydration ring-closing catalyst.

The polyimide solution thus obtained, may be used by itself, or may be precipitated and isolated in a poor solvent such as methanol or ethanol, and then it may be used as re-dissolved in a proper solvent. The solvent for re-dissolution is not particularly limited so long as it is capable of dissolving the polyimide, but as an example, 2-pyrorridone, N-methyl pyrrolidone, N-ethyl pyrrolidone, N-vinyl pyrrolidone, N,N-dimethyl acetoamide, N,N-dimethylformamide or γ-butyrolactone may be mentioned.

Further, even a solvent which is incapable of dissolving this polyimide by itself, may be added to the above solvent within a range not to impair the solubility. As such an example, ethyl cellosolve, butyl cellosolve, ethyl carbitol, butyl carbitol, ethyl carbitol acetate or ethylene glycol may be mentioned.

Further, for the purpose of further improving the adhesion of the polyimide film to the substrate, it is of course preferred to add an additive such as a coupling agent to the obtained polyimide solution.

This solution is coated on a substrate, and the solvent is evaporated, whereby a polyimide coating film can be formed on the substrate. The temperature at that time may be sufficient so long as the solvent can be evaporated, and usually a temperature of from 80 to 150° C. is sufficient.

Further, when it is used as a liquid crystal alignment film, a polyimide film having a film thickness of from 100 to 3000 Å, is formed on a transparent substrate of e.g. glass or plastic film provided with transparent electrodes, and then, the polyimide film is, subjected to rubbing treatment to obtain a liquid crystal alignment film.

BEST MODE FOR CARRYING OUT THE INVENTION

Now, the present invention will be described in further detail with reference to Examples, but the present invention is by no means restricted to such Examples.

Syntheses of Diamines

EXAMPLE 1

(Synthesis of n-dodecyl[3,5-bis(4-aminobenzoylamino)] benzoate) (4)

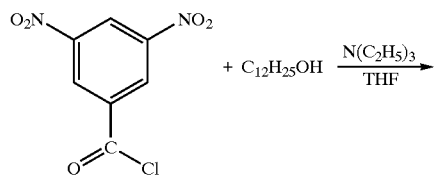

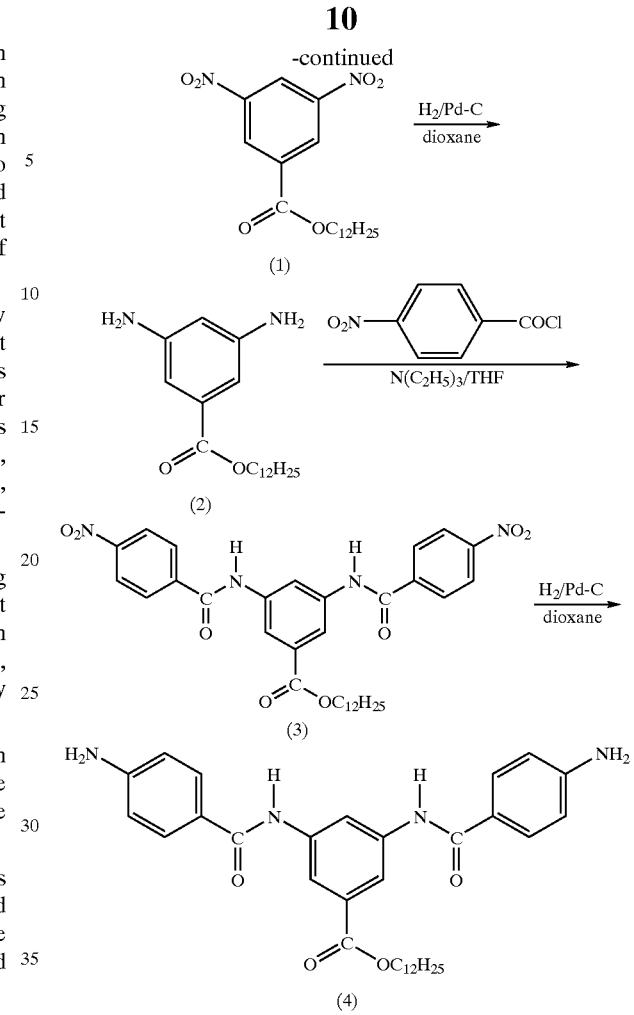

Into a 500 ml flask, 1-dodecanol (65.01 g, 348.9 mmol), triethylamine (44.00 g, 435.0 mmol) and tetrahydrofuran (410 ml) were added to obtain a uniform solution, and then, a THF solution (80 ml) of 3,5-benzoyl chloride (80.16 g, 347.7 mmol) was dropwise added. Thereafter, refluxing and stirring were continued for 2.5 hours. The reaction solution was poured into water, and the precipitated solid was separated by filtration and re-crystallized from acetonitrile to obtain colorless crystals (121.12 g, yield: 82%). From the IR and NMR spectra, the crystals were confirmed to be n-dodecyl-3,5-dinitrobenzoate (1). Melting point: 64° C.

Dioxane (250 ml) was added to n-dodecyl-3,5-dinitrobenzoate (1) (25.13 g, 59.2 mmol), and to this solution, Pd—C (1.51 g) was added in a nitrogen atmosphere, followed by stirring for 7 hours in a hydrogen atmosphere. Pd—C was filtered off, and the filtrate was poured into water, and the precipitated crystals were corrected by filtration. After drying, they were re-crystallized from n-hexane to obtain slightly yellow crystals (18.46 g, yield: 79%). From the IR and NMR spectra, the crystals were confirmed to be n-dodecyl-3,5-diaminobenzoate (2). Melting point 64° C.

Into a 200 ml flask, n-dodecyl-3,5-diaminobenzoate (2) (8.01 g, 20.3 mmol), triethylamine (4.57 g, 45.2 mmol) and tetrahydrofuran (100 ml) were added to obtain a uniform solution, and then, a THF solution (50 ml) of 4-nitrobenzoyl chloride (7.93 g, 42.8 mmol) was dropwise added. Thereafter, refluxing and stirring were continued for 6 hours. The reaction solution was poured into water, and the precipitated solid was collected by filtration and recrystallized from acetonitrile to obtain slightly yellow crystals (10.15 g, yield: 81%). From the IR and NMR spectra, the crystals were found to be n-dodecyl[3,5-bis(4-nitrobenzoylamino)]benzoate (3).

Melting point: 189° C.

Dioxane (160 ml) was added to n-dodecyl[3,5-bis(4-nitrobenzoylamino)]benzoate (3) (7.99 g, 12.9 mmol), and to this solution, Pd—C (0.87 g) was added in a nitrogen atmosphere, followed by stirring for 4 hours in a hydrogen atmosphere. Pd—C was filtered off, and then, the filtrate was poured into water, and the precipitated crystals were collected by filtration. After drying, they were recrystallized from THF-n-hexane to obtain slight yellow crystals (4.25 g, yield: 65%). From the IR and NMR spectra, these crystals were found to be the desired n-dodecyl[3,5-bis(4-aminobenzoylamino)]benzoate (4) (melding point: 186° C.).

The analytical results are shown below.

$^1$H-NMR (d-DMSO, δ ppm): 9.9 (2H, s), 8.6 (1H, s), 8.1 (2H, s), 7.8 (4H, d), 6.6 (4H, d), 5.8 (4H, s), 4.3 (2H, t), 1.7 (2H, m), 1.2–1.4 (18H, broad), 0.8 (3H, t).

IR (KBr, cm$^{-1}$): 3445, 3387, 3351 (NH$_2$), 3304, 3200 (NH), 2955, 2922, 2853 (CH$_2$), 1710 (COO), 1640, 1608 (CONH).

EXAMPLE 2
(Synthesis of n-hexyl[3,5-bis(4-aminobenzoylamino)]benzoate)

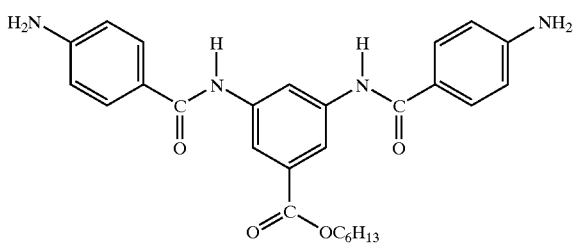

(5)

Using 3,5-dinitrobenzoyl chloride (74.3 g, 322.5 mmol) and hexyl alcohol (33.0 g, 323.6 mmol), n-hexyl-3,5-dinitrobenzoate was obtained (81.1 g, yield: 85%) in the same manner as in Example 1.

Using the obtained dinitro compound (33.4 g, 112.8 mmol), reduction was carried out in the same manner as in Example 1, followed by recrystallization to obtain n-hexyl-3,5-diaminobenzoate (25.6 g, yield: 96%).

Using n-hexyl-3,5-diaminobenzoate (24.0 g, 101.7 mmol) and 4-nitrobenzoyl chloride (39.7 g, 214.4 mmol), n-hexyl[3,5-bis(4-nitrobenzoylamino)]benzoate was obtained (44.5 g, yield: 82%) in the same manner as in Example 1.

Finally, this dinitro compound (20.4 g, 38.2 mmol) was reduced in the same manner as in Example 1, followed by recrystallization to obtain n-hexyl[3,5-bis(4-aminobenzoylamino)] (5) was obtained (14.8 g, yield: 82%).

Melding point: 208° C. The analytical results are shown below.

Mass (m/e): 474 (M+).

$^1$H-NMR (d-DMSO, δ ppm): 9.9 (2H, s), 8.6 (1H, s), 8.1 (2H, s), 7.8 (4H, d), 6.6 (4H, d), 5.8 (4H, s), 4.3 (2H, t), 1.7 (2H, m), 1.2–1.4 (6H, broad), 0.9 (3H, t).

IR (KBr, cm$^{-1}$): 3445, 3339, 3351 (NH$_2$), 3304, 3204 (NH), 2955, 2931 (CH$_2$), 1694 (COO), 1645, 1605 (CONH).

EXAMPLE 3
(Synthesis of n-hexadecyl[3,5-bis(4-aminobenzoylamino)]benzoate (6))

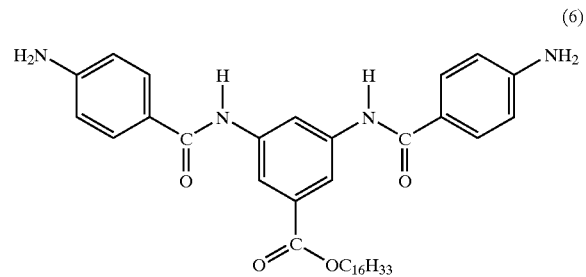

(6)

Using 3,5-dinitrobenzoyl chloride (60.6 g, 263.0 mmol) and hexadecyl alcohol (63.9 g, 263.9 mmol), n-hexadecyl-3,5-dinitrobenzoate was obtained (103.2 g, yield: 90%) in the same manner as in Example 1.

Using the obtained dinitro compound (40.68 g, 93.3 mmol), reduction was carried out in the same manner as in Example 1, followed by recrystallization to obtain n-hexadecyl-3,5-diaminobenzoate (35.0 g, yield: 100%).

Using the diamine compound (16.7 g, 44.4 mmol) and 4-nitrobenzoyl chloride (17.3 g, 93.6 mmol), n-hexadecyl [3,5-bis(4-nitrobenzoylamino)]benzoate was obtained (25.4 g, yield: 85%) in the same manner as in Example 1.

Finally, this dinitro compound (13.4 g, 19.9 mmol) was reduced in the same manner as in Example 1, followed by recrystallization to obtain n-hexadecyl[3,5-bis(4-aminobenzoylamino)] (6) was obtained (12.0 g, yield: 98%).

Melting point: 139° C. The analytical results are shown below.

Mass (m/e): 614 (M+).

$^1$H-NMR (d-DMSO, δ ppm): 10.0 (2H, s), 8.6 (1H, s), 8.1 (2H, s), 7.8 (4H, d), 6.6 (4H, d), 5.8 (4H, s), 4.3 (2H, t), 1.7 (2H, m), 1.2–1.4 (26H, broad), 0.8 (3H, t).

IR (KBr, cm$^{-1}$): 3388, 3346 (NH$_2$), 3304, 3204 (NH), 2952, 2917, 2834 (CH$_2$), 1708 ((COO) 1645, 1609 (CONH).

EXAMPLE 4
(Synthesis of n-dodecyl[3,5-bis(4-aminophenoxy)]benzoate) (10))

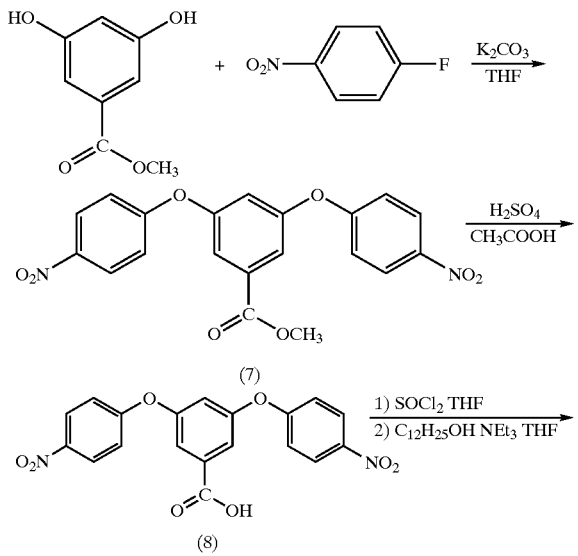

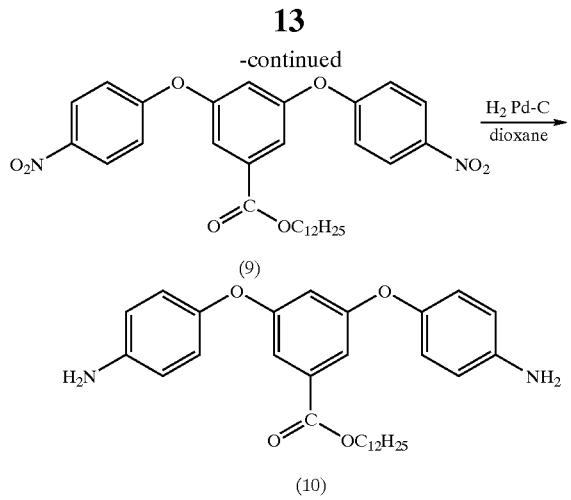

Into a 500 ml flask, 3,5-dihydroxymethyl benzoate (40.0 g, 238.1 mmol) obtained by a usual method, 4-fluoronitrobenzene (67.1 g, 475.8 mmol), potassium carbonate (65.4 g) and dimethylacetamide (350 ml) were added, followed by stirring at 95° C. for 9 hours. The reaction solution was subjected to filtration, and the filtrate was left to stand for one day. The precipitated solid was collected by filtration and recrystallized from ethyl acetate to obtain colorless solid 3,5-bis(4-nitrophenoxy)methyl benzoate (7) (78.5 g, yield: 80%).

Melting point: 183° C.

Into a 1 l flask, the above dinitro compound (70.0 g, 170.7 mmol), sulfuric acid (17.5 g) and acetic acid (600 ml) were put, followed by refluxing and stirring for 8 hours. The reaction solution was left to stand for one day, and the precipitated solid was collected by filtration. Recrystallization from acetic acid was carried out to obtain 3,5-bis(4-nitrophenoxy) benzoate (8) as colorless crystals (59.3 g, yield: 87%). Melting point: 230° C.

Into a 500 ml flask, 3,5-bis(4-nitrophenoxy) benzoate (8) (45.0 g, 114.0 mmol) and thionyl chloride (250 ml) were put, and refluxed and stirred for 3 hours. After completion of the reaction, excess thionyl chloride was removed by distillation, and THF (400 ml) was added to the residue. This THF solution was dropwise added at 80° C. to a THF solution (100 ml) of n-dodecyl alcohol (23.5 g, 126.3 mmol) and triethylamine (12.7 g, 125.7 mmol). After completion of the dropwise addition, refluxing and stirring were carried out for 15 hours. The solution was concentrated and poured into water (1500 ml) and extracted with ethyl-acetate. The organic layer was washed with water and 1N sodium hydroxide and dried over anhydrous sodium sulfate. Further, the solvent was distilled off under reduced pressure, and the residue was recrystallized from acetonitrile to obtain n-dodecyl[3,5-bis(4-nitrophenoxy)]benrzoate) (9) (47.6 g, yield: 74%).

Melting point: 64° C.

Dioxane (3,00 ml) was added to n-dodecyl[3,5-bis(4-nitrophenoxy)]benzoate (9) (15.7 g, 27.8 mmol), and to this solution, Pd—C (1.7 g) was added in a nitrogen atmosphere, followed by stirring for 6 hours in a hydrogen atmosphere. Pd—C was filtered off, and the filtrate was poured into water, and the precipitated crystals were collected by filtration. After drying, they were recrystallized from acetonitrile to obtain slight yellow crystals (9.00 g, yield: 65%). Melting point: 49° C. From the IR, NMR and Mass spectra, the crystals were found to be the desired n-dodecyl[3,5-bis(4-aminobenzoylamino)]benzoate (10). The analytical results are shown below.

Mass (m/e): 504 (M+).

$^1$H-NMR (d-DMSO, δ ppm): 7.2 (2H, s), 6.9 (4H, d), 6.7 (1H, s), 6.6 (4H, d), 4.2 (2H, t), 3.8 (4H, s), 1.6 (2H, m), 1.1–1.3 (18H, broad), 0.9 (3H, t).

IR (KBr, cm$^{-1}$): 3459, 3374 (NH$_2$), 3304, 3200 (NH), 2959, 2917, 2847 (CH$_2$), 1708 (COO), 1216 (ArO).

EXAMPLE 5
(Synthesis of n-hexadecyl[3,5-bis(4-aminobenzoylamino)] benzoate (11))

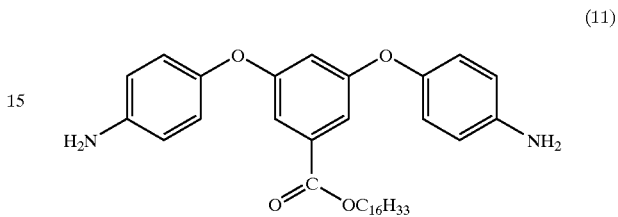

Using 3,5-bis(4-nitrophenoxy)benzoate (8) (25.6 g, 64.6 mmol) obtained in Example 4 and n-hexadecyl alcohol (17.3 g, 71.5 mmol), n-hexadecyl[3,5-bis(4-nitrophenoxy)]benzoate was obtained (32.4 g, yield: 81%) in the same manner as in Example 4.

Finally, this dinitro compound (16.4 g, 26.5 mmol) was reduced in the same manner as in Example 4, followed by recrystallization to obtain n-hexadecyl[3,5-bis(4-aminophenoxy)]benzoate (11) (13.5 g, yield: 91%). The melting point: 54° C. The analytical results are shown below.

Mass (m/e): 560 (M+).

$^1$H-NMR (d-DMSO, δ ppm): 7.2 (2H, s), 6.8 (4H, d), 6.6 (1H, s), 6.5 (4H, d), 4.2 (2H, t), 3.8 (4H, s), 1.6 (2H, m), 1.1–1.4 (26H, broad), 0.9 (3H, t).

IR (KBr, cm$^{-1}$): 3460, 3376 (NH$_2$), 3302, 3200 (NH), 2960, 2917, 2847 (CH$_2$), 1708 (COO), 1216 (ArO).

EXAMPLE 6
(Preparation of a Polyimide)

5 g (10.5 mmol) of n-dodecyl[3,5-bis(4-aminobenzoylamino)]benzoate obtained in Example 1 and 2.1 g (10.5 g) of 1,2,3,4-cyclobutanetetracarboxylic dianhydride were dissolved in 40 g of N-methylpyrrolidone, followed by stirring at 20° C. for 8 hours to carry out a polycondensation reaction to obtain a polyimide precursor solution.

The reduced viscosity of the obtained polyimide precursor was 0.80 dl/g (at a concentration of 0.5 g/dl in N-methylpyrrolidone at 30° C.).

This solution was heat-treated at 180° C. for one hour to obtain a uniform polyimide coating film. The obtained coating film was subjected to IR measurement and was confirmed to be a polyimide having a dodecyl group.

EXAMPLE 7

5 g (10.5 mmol) of n-dodecyl[3,5-bis(4-aminobenzoylamino)]benzoate obtained in Example 1 and 2.6 g (10.5 mmol) of bicyclo[3,3,0]-octane-tetracarboxylic dianhydride were dissolved in 40 g of N-methylpyrrolidone, followed by stirring at 20° C. for 8 hours to carry out a polycondensation reaction to obtain a polyimide precursor solution. The reduced viscosity of the obtained polyimide precursor was 0.70 dl/g (at a concentration of 0.5 g/dl in N-methylpyrrolidone at 30° C.).

To this solution, acetic anhydride and pyrimidine were added as an imide conversion catalyst, followed by a reaction at 60° C. for one hour to obtain a soluble polyimide resin solution. This solution was put into methanol, and the obtained precipitate was collected by filtration and dried to obtain a white polyimide powder.

This polyimide resin powder was confirmed to be 70% imide-converted, by NMR. Further, the obtained coating film was subjected to IR measurement and was confirmed to be a polyimide having a dodecyl group.

EXAMPLE 8

5 g (10.5 mmol) of n-dodecyl[3,5-bis(4-aminobenzoylamino)]benzoate obtained in Example 1 and 2.9 g (10.5 mmol) of 3,4-dicarboxy-1,2,3,4-tetrahydro-1-naphthalene succinic dianhydride were dissolved in 40 g of N-methylpyrrolidone, followed by stirring at 20° C. for 8 hours to carry out a polycondensation reaction to obtain a polyimide precursor solution. The reduced viscosity of the obtained polyimide precursor was 0.75 dl/g (at a concentration of 0.5 g/dl in N-methylpyrrolidone at 30° C.)

To this solution, acetic anhydride and pyrimidine were added as an imide-conversion catalyst, followed by a reaction at 60° C. for one hour to obtain a soluble polyimide resin solution. This solution was put into 500 g of methanol, and the obtained precipitate was collected by filtration and dried to obtain a white polyimide powder.

This polyimide resin powder was confirmed to be 90% imide-converted, by NMR. Further, the obtained coating film was subjected to IR measurement and confirmed to be a polyimide having a dodecyl group.

EXAMPLE 9

5 g (10.5 mmol) of n-dodecyl[3,5-bis(4-aminobenzoylamino)]benzoate obtained in Example 1 and 2.6 g (10.5 mmol) of 3,5,6-tricarboxynorbornene-2:3,5:6 dianhydride were dissolved in 40 g of N-methylpyrrolidone, followed by stirring at 20° C. for 8 hours to carry out a polycondensation reaction to obtain a polyimide precursor solution. The reduced viscosity of the obtained polyimide precursor was 0.55 dl/g (at a concentration of 0.5 g/dl in N-methylpyrrolidone at 30° C.).

To this solution, acetic anhydride and pyridine were added as an imide conversion catalyst, followed by a reaction at 60° C. for one hour to obtain a soluble polyimide resin solution. This solution was put into 500 g of methanol, and the obtained precipitate was collected by filtration and dried to obtain a white polyimide powder.

This polyimide resin powder was confirmed to be 90% imide-converted, by NMR. Further, the obtained coating film was subjected to IR measurement and confirmed to be a polyimide having a dodecyl group.

EXAMPLES 10 to 20

Using the diamines synthesized in Examples 2 to 5 and using tetracarboxylic dianhydrides employed in Examples 6 to 9, polyimides were synthesized in accordance with the respective Examples, and subjected to IR measurements in accordance with Example 6 and confirmed to be the desired polyimides. In the following Table 1, the reduced viscosities of the precursor solutions of the polyimides (at a concentration of 0.5 g/dl in N-methylpyrrolidone at 30° C.) will be given.

TABLE 1

| Example No. | Diamine | Tetracarboxylic dianhydride | Reduced viscosity (dl/g) |
| --- | --- | --- | --- |
| 10 | Example 2 | Example 6 | 1.05 |
| 11 | Example 2 | Example 7 | 0.82 |
| 12 | Example 2 | Example 8 | 0.77 |
| 13 | Example 2 | Example 9 | 0.60 |
| 14 | Example 3 | Example 6 | 0.74 |
| 15 | Example 3 | Example 7 | 0.75 |
| 16 | Example 3 | Example 8 | 0.65 |
| 17 | Example 3 | Example 9 | 0.53 |
| 18 | Example 4 | Example 6 | 1.14 |
| 19 | Example 4 | Example 7 | 0.96 |
| 20 | Example 4 | Example 8 | 0.88 |
| 21 | Example 4 | Example 9 | 0.67 |
| 22 | Example 5 | Example 6 | 1.03 |
| 23 | Example 5 | Example 7 | 0.89 |
| 24 | Example 5 | Example 8 | 0.83 |
| 25 | Example 5 | Example 9 | 0.60 |

COMPARATIVE EXAMPLE 1

5 g (14.3 mmol) of hexadecyloxy-2,4-diaminobenzene as a diamine and 2.8 g (14.3 mmol) of 1,2,3,4-cyclobutanetetracarboxylic dianhydride were dissolved in 40 g of N-methylpyrrolidone, followed by stirring at 20° C. for 8 hours to carry out a polycondensation reaction to obtain a polyimide precursor solution. The reduced viscosity of the obtained polyimide precursor was as low as 0.35 dl/g (at a concentration of 0.5 g/dl in N-methylpyrrolidone at 30° C.).

COMPARATIVE EXAMPLE 2

5 g (14.3 mmol) of hexadecyloxy-2,4-diaminobenzene as a diamine and 3.6 g (14.3 mmol) of bicyclo[3,3,0]-octane-tetracarboxylic dianhydride were dissolved in 40 g of N-methylpyrrolidone, followed by stirring at 20° C. for 4 hours to carry out a polycondensation reaction, but polymerization did not substantially proceed, and only an oligomer was formed. Further, heating was carried out, but no improvement in effects was observed.

COMPARATIVE EXAMPLE 3

5 g (14.3 mmol) of hexadecyloxy-2,4-diaminobenzene as a diamine and 4.3 g (14.3 mmol) of 3,4-dicarboxy-1,2,3,4-tetrahydro-1-naphthalene succinic dianhydride were dissolved in 40 g of N-methylpyrrolidone, followed by stirring at 20° C. for 4 hours to carry out a polycondensation reaction, but polymerization did not substantially proceed, and only an oligomer was formed. Further, heating was carried out, but no improvement in effects was observed.

COMPARATIVE EXAMPLE 4

5 g (14.3 mmol) of hexadecyloxy-2,4-diaminobenzene as a diamine and 3.6 g (14.3 mmol) of 3,5,6-tricarboxynorbornane-2:3,5:6 dianhydride were dissolved in 40 g of N-methylpyrrolidone, followed by stirring at 20° C. for 4 hours to carry out a polycondensation reaction, but polymerization did not substantially proceed, and only an oligomer was formed. Further, heating was carried out, but no improvement in effects was observed.

EXAMPLES 26 to 45
(Preparation of Liquid Crystal Alignment Films)

Then, a polyimide precursor or a polyimide solution obtained in one of Examples 6 to 25 was coated on a glass substrate and heat-treated at 180° C. to form a polyimide coating film, whereupon the tilt angle and the uniformity in alignment of liquid crystal when used as a liquid crystal alignment film, were measured in accordance with the following methods.

Evaluation of the tilt angle: a polyimide precursor or a polyimide solution obtained in one of Examples 6 to 21 and Comparative Example 1 was diluted with N-methylpyrrolidone or γ-butyrolactone to obtain a solution having a resin concentration of 5%, which was spin-coated on a transparent electrode-mounted glass substrate at a rotational speed of 3500 rpm and heated at 80° C. for 10 minutes and at 250° C. for one hour to obtain a uniform polyimide coating film. After rubbing this coating film with a cloth, such substrates were assembled so that the rubbing directions were in parallel, with a spacer of 23 μm interposed, and liquid crystal (ZLI-2003, manufactured by Merck Company) was injected to prepare a cell having homeotropic or homogeneous alignment.

With respect to this cell, after heat treatment at 120° C. for one hour, the uniformity of liquid crystal alignment under a polarization microscope was confirmed, and the tilt angle was measured by a crystal rotation method or a magnetic field quantitative method. The results are shown in Table 2.

TABLE 2

| Example No. | Polyimide (Example No.) | Diamine (Example No.) | Tilt angle (°) | Uniformity of alignment |
|---|---|---|---|---|
| 26 | 6* | 1 | 90 | Uniform |
| 27 | 7 | 1 | 90 | Uniform |
| 28 | 8 | 1 | 90 | Uniform |
| 29 | 9 | 1 | 90 | Uniform |
| 30 | 11* | 2 | 6 | Uniform |
| 31 | 11 | 2 | 2 | Uniform |
| 32 | 12 | 2 | 3 | Uniform |
| 33 | 13 | 2 | 3 | Uniform |
| 34 | 14* | 3 | 90 | Uniform |
| 35 | 15 | 3 | 90 | Uniform |
| 36 | 16 | 3 | 90 | Uniform |
| 37 | 17 | 3 | 90 | Uniform |
| 38 | 18* | 4 | 90 | Uniform |
| 39 | 19 | 4 | 90 | Uniform |
| 40 | 20 | 4 | 90 | Uniform |
| 41 | 21 | 4 | 90 | Uniform |
| 42 | 22* | 5 | 90 | Uniform |
| 43 | 23 | 5 | 90 | Uniform |
| 44 | 24 | 5 | 90 | Uniform |
| 45 | 25 | 5 | 90 | Uniform |
| Comp. Ex. 1 | | 1 | 90 | Non-uniform |

*The polyimide precursor solution was employed.

INDUSTRIAL APPLICABILITY

The diaminobenzene derivative of the present invention can easily be synthesized and irrespective of the structure of the acid dianhydride, it has a high reactivity for swift polymerization, whereby the corresponding polyimide having a high molecular weight can easily be obtained. Further, in the case of a polyimide for an alignment film for a liquid crystal display device, it is capable of aligning liquid crystal uniformly, whereby a desired tilt angle can easily be obtained.

What is claimed is:

1. A liquid crystal alignment film containing a polyimide obtained by reacting a diamine containing at least 1 mol % of a diaminobenzene derivative represented by the general formula (1):

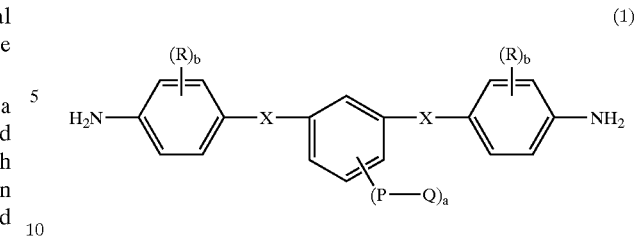

(1)

[wherein each of X and P which are independent of each other, is a single bond or a bivalent organic group selected from —O—, —COO—, —OCO—, —CONH— and —NHCO—, Q is a $C_{1-22}$ straight chain alkyl group or straight chain fluoroalkyl group with the proviso that when X is oxygen, P cannot be a single bond, a is an integer of from 1 to 4 and represents the number of substituents, R is a substituent selected from fluorine, a methyl group and a trifluoromethyl group, and b is an integer of from 0 to 4 and represents the number of substituents], with at least one compound selected from a tetracarboxylic dianhydride and its derivatives, to obtain a polyimide precursor having a reduced viscosity of from 0.05 to 5.0 dl/g [in N-methylpyrrolidone at a temperature of 30° C., concentration: 0.5 g/dl] and ring-closing it, and having a repeating unit represented by the general formula (2):

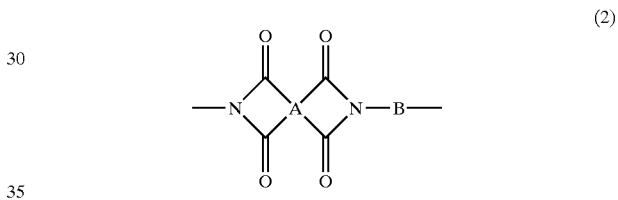

(2)

[wherein A is a tetravalent organic group constituting a tetracarboxylic acid, and B is a bivalent organic group constituting a diamine].

2. The liquid crystal alignment film according to claim 1, wherein the tetracarboxylic dianhydride is an alicyclic tetracarboxylic dianhydride.

3. The liquid crystal alignment film according to claim 2, wherein the alicyclic tetracarboxylic dianhydride is at least one tetracarboxylic dianhydride selected from 1,2,3,4-cyclobutane tetracarboxylic dianhydride, bicyclo[3,3,0]-octane tetracarboxylic dianhydride, 3,4-dicarboxy-1,2,3,4-tetrahydro-1-naphthalene succinic dianhydride and 3,5,6-tricarboxynorbornane-2:3,5:6 dianhydride.

4. The liquid crystal alignment film according to claim 1, wherein

X is a single bond or a bivalent organic group selected from —COO—, —OCO—, —CONH— and —NHCO—; and P is a single bond or a bivalent organic group selected from —O—, —COO—, —OCO—, —CONH— and —NHCO—.

5. The liquid crystal alignment film according to claim 1, wherein X is a single bond.

6. The liquid crystal alignment film according to claim 1, wherein X is a bivalent organic group selected from —COO—, —OCO—, —CONH— and —NHCO—.

7. The liquid crystal alignment film according to claim 1, wherein X is a —COO— group.

8. The liquid crystal alignment film according to claim 1, wherein X is a —OCO— group.

9. The liquid crystal alignment film according to claim 1, wherein X is a —CONH— group.

10. The liquid crystal alignment film according to claim 1, wherein X is a —NHCO— group.

11. The liquid crystal alignment film according to claim 1, wherein P is a single bond.

12. The liquid crystal alignment film according to claim 1, wherein P is a —O— group.

13. The liquid crystal alignment film according to claim 1, wherein P is a bivalent organic group selected from —COO—, —OCO—, —CONH— and —NHCO—.

14. The liquid crystal alignment film according to claim 1, wherein P is a —COO— group.

15. The liquid crystal alignment film according to claim 1, wherein P is a —OCO— group.

16. The liquid crystal alignment film according to claim 1, wherein P is a —CONH— group.

17. The liquid crystal alignment film according to claim 1, wherein P is a —NHCO— group.

* * * * *